US00PP08123P

United States Patent [19]

Jessel, Jr.

[11] Patent Number: Plant 8,123

[45] Date of Patent: Feb. 2, 1993

[54] CARNATION PLANT NAMED CFPC CHERIÉ

[75] Inventor: Walter H. Jessel, Jr., Salinas, Calif.

[73] Assignee: California Florida Plant Co., L.P., Salinas, Calif.

[21] Appl. No.: 678,853

[22] Filed: Mar. 28, 1991

[51] Int. Cl.[0] ..... A01H 5/00

[52] U.S. Cl. ..... Plt./72.1

[58] Field of Search ..... Plt./70.1, 71.1, 72.1, Plt./73.1

*Primary Examiner*—Howard J. Locker

*Attorney, Agent, or Firm*—Christie, Parker & Hale

[57] ABSTRACT

A new and unusal carnation of pink coloration.

1 Drawing Sheet

SUMMARY OF THE INVENTION

The present invention relates to a nev' and distinct variety of carnation plant which was originated by me in a controlled breeding program by my crossing as seed and pollen parents, two unnamed and unpatented seedlings of my creation. The varietal denomination of this new carnation is 'CFPC Cherié'.

Among the novel characteristics possessed by the new variety which distinguishes it from its parents and all other varieties of which I am aware, including the variety 'Katia' which is closest to the new variety, are its attractive pink flower coloring and resistance to soil-borne and air borne diseases as well as to thrip. The new variety provides fast flowering response about 15 to 16 weeks from planting to flowering, good vase-life and improved flower form with less reflexing and twisting of petals.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows a typical specimen of the flowers of the new variety depicted in color as nearly true as it is reasonably possible to make the same in a color illustration of this character.

DESCRIPTION OF THE NEW VARIETY

The new variety, CFPC Cherié is resistant to soil-borne and air-borne diseases such as alternaria and root rots such as damping-off, water molds and the like. In comparison to the closest known variety 'Katia', CFPC Cherié displays less calyx splitting, four to five weeks faster flowering (from same planting date) and flowers of CFPC Cherié have fewer markings of other colors, e.g. purple, orange, light pink. The new variety has more petals and 1 to 2 more lobes of calyx than 'Katia' as well as less thrip sensitivity and more even coloration. The attractive pink coloring and the other characteristics heretofore and hereinafter described, make CFPC Cherié especially suitable for commercial cut flower production.

The following is a detailed description of my new variety, with color terminology in accordance with The Royal Horticultural Society Colour Chart (RHSCC). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouse at Fremont, Calif. The height of plant and flower and foliage size are established as an average using standard commercial cultural practices.

Name: CFPC Cherié.

Classification:

*Botanical.*—Dianthus caryophyllus.

*Commercial.*—Carnation, standard disbud type.

Parentage:

*Female parent.*—Unnamed seedling (No. 820011).

*Male parent.*—Unnamed seedling (No. 830063).

Plant:

*Height.*—About 34 inches.

*Growing habit.*—Herbaceous, semi-upright.

*Blooming habit.*—Terminal as a disbud.

*Blooming season.*—Year round.

*Rooting time.*—17 days.

*Mutation prone.*—No.

*Disease resistance.*—Alternaria sp.

*Temperature tolerance.*—Typical for carnation.

Foliage:

*Color.*—Upper side: Near to 137A.

Lower side: Near to 137A.

*Size.*—About 3-¼ to 4-¼ inches.

*Quantity.*—Numerous.

*Shape.*—Lanceolate.

*Texture.*—Smooth.

*Ribs.*—Central, keeled.

*Arrangement.*—Bi-lateral.

Bloom:

*Form.*—Circular, high.

*Shape.*—Round.

*Size.*—Diameter average: About 3 to 3⅜ inches. Depth average: About 1¼ to 1½ inches.

*Borne.*—Terminally as a standard

*Color.*—General tonality: Dark Pink, near to 52D to B, however, depending on available light coloration may extend to near 57 to 63C.

*Permanence.*—Yes (dry up).

*Keeping habit.*—10 to 12 days.

*Fragrance.*—Slight.

Petals:

*Number.*—Average about 98.

*Outer petals.*—Length: About 2½ inches. Width: About 1⅛ inches.

*Central petals.*—Length: About 1⅞ inches. Width: About ½ inch.

*Texture.*—Smooth.

*Form.*—Fan shaped.

Reproductive organs:

*Filaments.*—White, about ⅝ to ¾-inches.

*Styles.*—White.

*Anthers.*—Light tan.

*Ovaries.*—Shape: Conical. Color: Green at base, tan at apex.

*Stigma.*—Pinkish white.

*Pollen.*—No pollen evident.

I claim:

1. A new and distinct variety of carnation plant, substantially as shown and described, characterized particularly by flowers of attractive pink coloration.

* * * * *

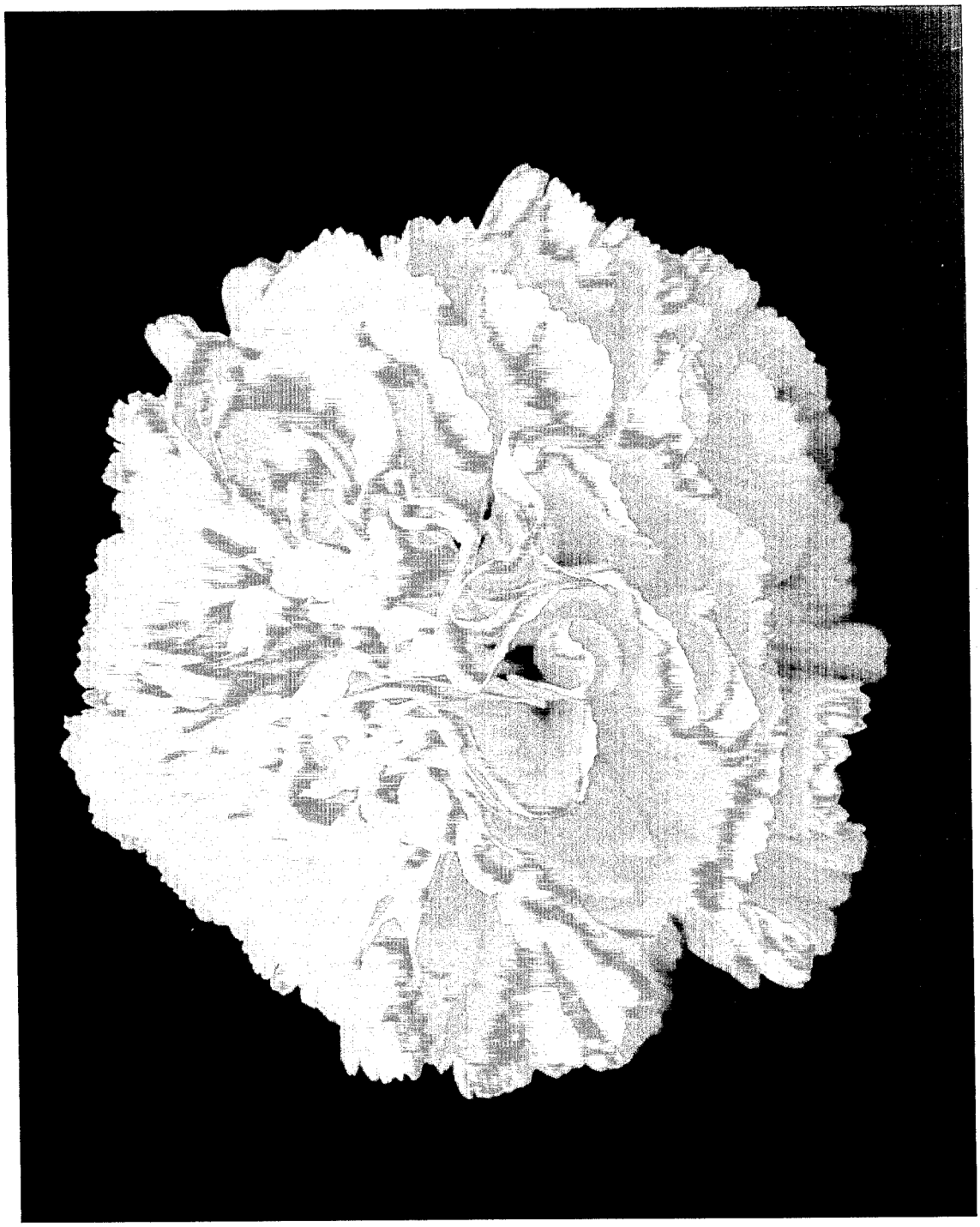

UNITED STATES PATENT AND TRADEMARK OFFICE

CERTIFICATE OF CORRECTION

PATENT NO. : Plant 8,123

DATED : February 2, 1993

INVENTOR(S) : Walter H. Jessel, Jr.

It is certified that error appears in the above-identified patent and that said Letters Patent is hereby corrected as shown below:

Column 3, line 4, change "57" to -- 57A --.

Signed and Sealed this

Fourteenth Day of December, 1993

*Attest:*

Bruce Lehman

BRUCE LEHMAN

*Attesting Officer*

*Commissioner of Patents and Trademarks*